United States Patent [19]
Nita et al.

[11] Patent Number: 5,542,917
[45] Date of Patent: Aug. 6, 1996

[54] ULTRASOUND DELIVERY CATHETERS INCORPORATING IMPROVED DISTAL TIP CONSTRUCTION

[75] Inventors: Henry Nita, Mission Viejo; Timothy Mills, Belvedere Tiburon, both of Calif.

[73] Assignee: Baxter International, Inc., Deerfield, Ill.

[21] Appl. No.: 324,450

[22] Filed: Oct. 18, 1994

Related U.S. Application Data

[60] Continuation-in-part of Ser. No. 127,985, Sep. 28, 1993, Pat. No. 5,405,318, which is a division of Ser. No. 878,795, May 5, 1992, Pat. No. 5,267,954, which is a continuation-in-part of Ser. No. 640,190, Jan. 11, 1991, Pat. No. 5,304,115, and Ser. No. 787,292, Nov. 4, 1991.

[51] Int. Cl.$^6$ ................................................. A61B 17/20
[52] U.S. Cl. ....................... 604/22; 606/159; 607/97
[58] Field of Search ........................ 604/21, 22, 52; 606/159, 169, 170, 171; 601/2; 128/662.03, 662.06; 607/97

[56] References Cited

U.S. PATENT DOCUMENTS

| | | | |
|---|---|---|---|
| 4,870,953 | 10/1989 | DonMicheal et al. | 128/24 |
| 5,248,296 | 9/1993 | Alliger | 604/22 |
| 5,267,954 | 12/1993 | Nita | 604/22 |
| 5,304,115 | 4/1994 | Russell et al. | 604/22 |

*Primary Examiner*—John D. Yasko
*Attorney, Agent, or Firm*—Fulwider Patton; Lee & Utecht

[57] ABSTRACT

Ultrasound delivery catheters comprising elongate flexible catheter bodies having rigid distal tip or head members inserted into, and affixed thereto. At least one ultrasound transmission member extends longitudinally through the catheter body and is coupled to the distal tip or head member. Additionally, the invention provides methods for manufacturing such ultrasound delivering catheters.

65 Claims, 4 Drawing Sheets

ULTRASOUND DELIVERY CATHETERS INCORPORATING IMPROVED DISTAL TIP CONSTRUCTION

RELATED APPLICATIONS

The present application is a continuation-in-part of U.S. patent application No. 08/127,985 filed Sep. 28, 1993, now U.S. Pat. No. 5,405,318 which is a division of Ser. No. 07/878,795, filed May 5, 1992, and subsequently issued as U.S. Pat. No. 5,267,954 on Dec. 7, 1993, said Pat. No. 5,267,954 being a continuation-in-part of Ser. No. 07/640,190 filed Jan. 11, 1991 now U.S. Pat. No. 5,304,115 and Ser. No. 07/787,292 filed Nov. 4, 1991 now pending.

FIELD OF THE INVENTION

The present invention relates generally to medical devices and more particularly to catheters for delivering ultrasonic energy to treatment sites within a mammalian body for purposes of ultrasonically treating or ablating unwanted tissue or matter.

BACKGROUND OF THE INVENTION

The prior art has included a number of ultrasonic catheters inserted into the mammalian body and usable to deliver ultrasonic energy for purposes of ablating obstructive material from anatomical cavities or passageways, or for other therapeutic purposes.

Examples of ultrasonic treatment catheters and related apparatus include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), 5,267,954 (Nita), and 5,100,423 (Fearnot) as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2,438,648 (Pohlman).

Additionally, ultrasound transmitting catheters may be utilized to deliver ultrasonic energy to mammalian blood vessels for the purpose of preventing or reversing vasospasm, as described in co-pending U.S. patent application Ser. No. 07/911,651, entitle ANGIOPLASTY AND ABLATIVE DEVICES HAVING ONBOARD ULTRASOUND COMPONENTS AND DEVICES AND METHODS FOR UTILIZING ULTRASOUND TO TREAT OR PREVENT VASOSPASM.

One particular type of ultrasound transmitting catheter which may be utilized to deliver therapeutic ultrasound to an intracorporeal treatment site comprises an elongate flexible catheter body having an ultrasound transmission member (e.g., a wire) extending longitudinally therethrough and terminate in an enlarged or bulbous distal tip member. One example of an ultrasound delivering catheter incorporating this type of catheter-body-attached distal tip member is described in U.S. patent application Ser. No. 08/127,985, of which this application is a continuation-in-part.

In view of the therapeutic usefulness of ultrasound-delivering catheters, there exists a need in the art for further invention, development and refinement of the previously known ultrasound catheters, so as to improve the operative characteristics, reliability and/or economy of such catheters. Also, it is desirable to devise new catheter designs and/or methods of manufacturing such catheter whereby the expense of such ultrasound delivering catheters may be minimized.

SUMMARY OF THE INVENTION

The present invention provides improved ultrasound delivery catheter devices comprising elongate tubular catheter bodies having rigid distal tip or head members inserted into, or affixed onto the distal end thereof. Additionally, the present invention provides methods for manufacturing such improved ultrasound delivering catheters.

In accordance with a first embodiment of the invention, an aperture is formed through a side wall of the rigid distal tip to form an opening into a guidewire bore which extends longitudinally through the distal tip member. Adhesive material is disposed within such aperture so as to form a three way bond between a) a guidewire tube positioned within said guidewire bore, b) the distal tip member and c) the pliable catheter body. The type of adhesive disposed within the aperture is selected so as to provide a firm adhesive bond between the guidewire tube, distal tip member and catheter body.

In accordance with a second embodiment of the invention, there is provided an ultrasound delivering catheter of the foregoing character wherein a rigid distal tip member is initially bonded to the distal end of the pliable catheter body by way of adhesive, and subsequently secured thereto by wrapping a wrapping member (e.g., thread or wire) around the distal portion of the catheter body so as to exert compressive force against the distal tip member, thereby enhancing the adhesive attachment of the distal tip member to the catheter body.

In accordance with a third embodiment of the invention, there is provided an ultrasound delivering catheter of the foregoing character wherein the rigid distal tip member is initially bonded to the catheter body by way of an adhesive and a band member is crimped or otherwise compressively attached about the outer surface of the catheter body so as to exert compressive force against the distal tip member, thereby compressively enhancing the adhesive bonding of the distal tip member to the catheter body.

In accordance with a fourth embodiment of the invention, there is provided an ultrasound delivering catheter of the foregoing character wherein the rigid distal tip member is specifically configured to include a barbed or otherwise fictionally engageable projection or portion which will engage the catheter body when the distal tip is affixed thereto. In this embodiment, the distal tip additionally includes a void or depression wherein an adhesive may be applied to adhesively bond the distal tip member to the catheter body.

The specific elements and attributes of each of the above described four (4) embodiments may be incorporated into separate physical embodiments as described, or may be combined in any possible permutations and/or combinations thereof.

Further objects and advantages of the present invention will become apparent to those skilled in the art upon reading and understanding of the following detailed description and the accompanying drawings.

DETAILED DESCRIPTION OF THE PREFERRED EMBODIMENTS

The following detailed description and the accompanying drawings are provided for purposes of describing and illustrating presently preferred embodiments of the invention only, and are not intended to limit the scope of the invention in any way.

i. Structural Attributes Common To All Embodiments of the Invention

Figure 1:
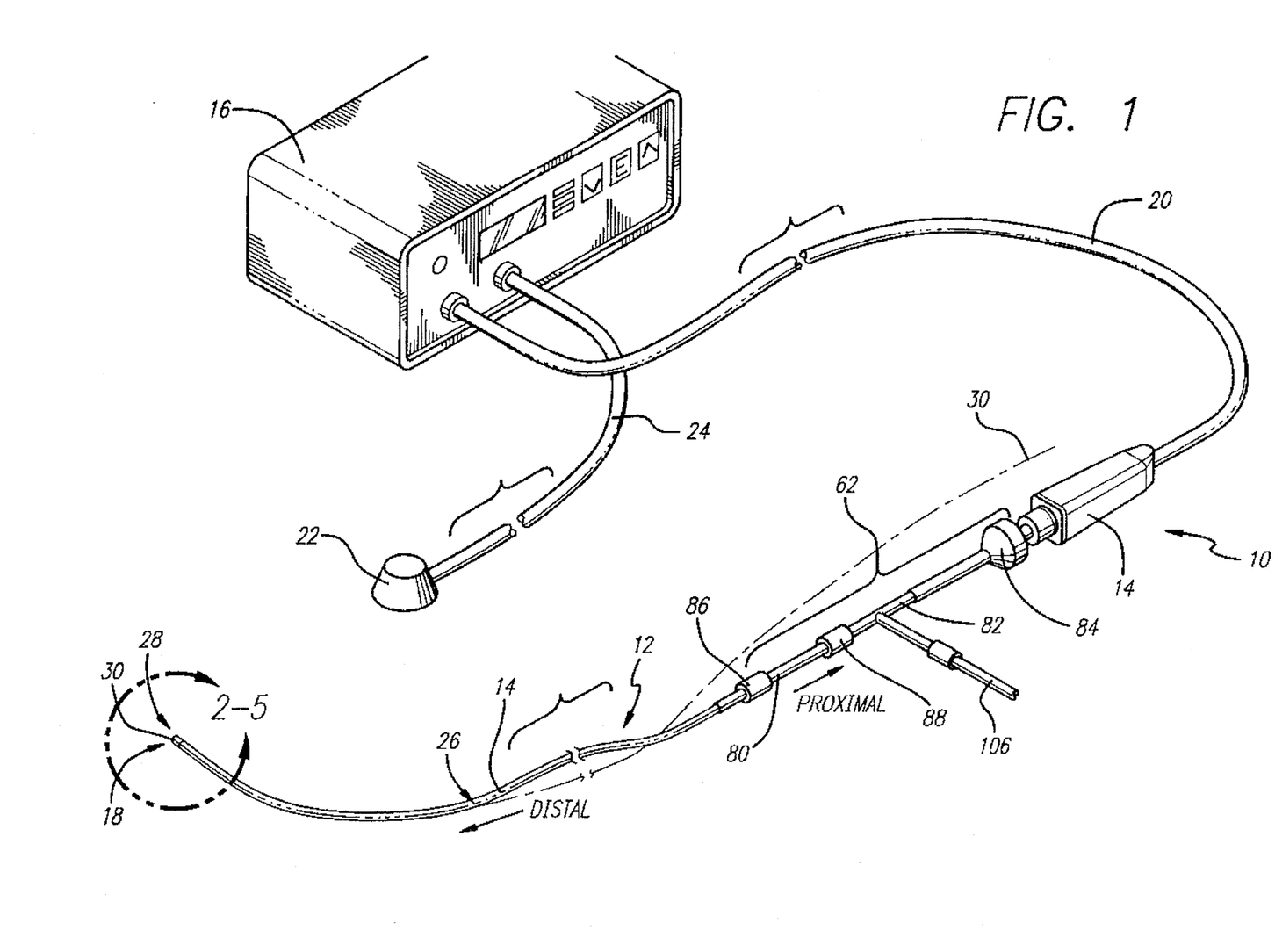
FIG. 1 is a general perspective view of an ultrasound delivering system incorporating an ultrasound delivery catheter of the present invention.

FIG. 1 is a general showing of an overall ultrasound system 10 of the present invention. The system 10 incorporates an ultrasound delivering catheter 12, an ultrasound transducer 14 and an electrical signal generator 16.

The ultrasound delivery catheter 12 comprises an elongate pliable catheter body 14 having a proximal end, a distal end and at least one ultrasound transmission member 16 extending longitudinally therethrough. A distal tip member 18 is mounted on the distal end of the pliable catheter body 14 and the elongate ultrasound transmission member 16 is connected to or in abutment with the distal tip member 18 so as to transmit ultrasonic vibration to the distal portion of the catheter body 14. A proximal connector assembly 62 is positioned on the proximal end of the catheter body 14. Such proximal connector assembly 62 is configured and constructed to facilitate operative connection of the proximal end of the ultrasound transmission member 16 to an ultrasound transducer 14 such that ultrasonic energy may be transmitted by the ultrasound transmission member 16, from the ultrasound transducer 14 to the distal end of the catheter 12.

The ultrasound transducer 14 is connected to the electrical signal generator 16 by way of cable 20 an on/off foot pedal switch 22 is connected to the electrical signal generator 16 by way of cable 24. By such arrangement, the on/off foot pedal switch 22 may be depressed to cause the signal generator 16 to emit an electrical signal through cable 20 to ultrasound transducer 14. The ultrasound transducer 14 is operative to convert the electrical signal into ultrasound energy at a frequency, and in a pattern which, when transmitted to the distal end of the catheter 12, will effect the intended therapeutic or ablative application.

On example of a signal generator 16 usable in conjunction with the system 10 of the present invention is that, which is available as Model UAG-1110, Baxter Healthcare Corporation, Interventional Cardiology Division, Irvine, Calif.

One ultrasound transducer 14 useable in the system 10 of the present invention is that which is available as Model UAT1000 from Baxter Healthcare Corporation, Interventional Cardiology Division, Irvine, Calif.

The catheter 12 shown in FIG. 1 is a "monorail" or "rapid exchange" type of catheter wherein a guide wire passageway extends longitudinally through a distal portion of the catheter body 14, between a first guide wire passage aperture 26 formed in the side wall of the catheter body 14 and a second guide wire passage aperture 28 formed in the distal tip member 18 at the distal end of the catheter body 14. By such an arrangement, a guide wire may be longitudinally advanced or retracted through the distal portion of the catheter body, and may be disposed adjacent to an outside of the proximal portion of the catheter body.

It will be appreciated that, in an alternative to the "monorail" design shown in FIG. 1, the catheter 12 of the present invention may also be configured as an "over-the-wire" catheter wherein a guide wire lumen extends longitudinally through the catheter body 14 and a guide wire entry/exit side arm (not shown) is formed on the proximal connector assembly 62 such that the guide 30 may be inserted through the entire length of the catheter 12, and is insertable/extractable through a side arm or aperture formed in the proximal connector assembly 62.

In many applications, it may be desirable for the catheter 12 to have optimal pliability or flexibility, especially in the distal portion of the catheter body 14, such that the catheter may be inserted into small or tortuous anatomical passageways without crimping of the catheter body or breakage/damage to the ultrasound transmission member 16. To facilitate such bendability or pliability of the catheter, while maintaining desirable ultrasound transmission properties, the ultrasound transmission member 16 may be formed of one or more materials which exhibit super elasticity in the range of operating temperatures encounter by the ultrasound transmission member 16 during the operation of the catheter 12. Specifically, all or part of the ultrasound transmission member 16 may be formed of metal alloys known as "shape memory alloys", such alloys exhibiting super elastic properties when maintained in a consistent crystalline state.

Examples of super elastic metal alloys which are usable to form the ultrasound transmission member 16 are described in detail in U.S. Pat. Nos. 4,665,906 (Jervis); 4,565,589 (Harrison); 4,505,767 (Quin) and 4,337,090 (Harrison), the disclosures of such U.S. Patents being expressly incorporated herein by reference insofar as they describe the compositions, properties, chemistries and behaviors of specific metal alloys which may exhibit desirable super elastic properties within the temperature range at which the ultrasound transmission member 16 of the catheter 12 is required to operate.

In particular, one presently preferred super elastic metal alloy of which the ultrasound transmission member 16 may be formed is a nickel-titanium alloy made of 55.8 weight percent (50.8 atomic percent) nickel/balance titanium, and commercially available as TINEL™ BB from RayChem Corporation, Menlo Park, Calif.

The physical properties of the preferred 50.8 atomic percent nickel-titanium alloy are as follow:

| Properties of NiTi Alloy Having 50.8 At. % Nickel/Balance Titanium | | |
|---|---|---|
| Property * | Units | Value |
| Superelastic Temperature Range | °C. | 20 to 80 |
| Loading Plateau Stress (at 20° C.) | Mpa | 480 |
| Unloading Plateau Stress | Mpa | 135 |
| Permanent Set (at 20° C. after 8% strain) | % | 0.2 |
| Ultimate Tensile Strength (at 20° C.) | Mpa | 1150 |
| | Ksi | 170 |
| Elongation at Failure | % | 10 |
| Melting Point | °C. | 1350 |
| Density | g/cm | 6.5 |
| | lbs/cu. Inch | 0.235 |

* Typical Values for Cold Worked and Shape Set Condition

The proximal connector assembly 62 on the proximal end of the catheter 12 may be configured and constructed in many different ways to accomplish the desired function of operatively coupling the ultrasound transmission member 16 of the catheter 12 to the ultrasound transducer 14.

Figure 6:
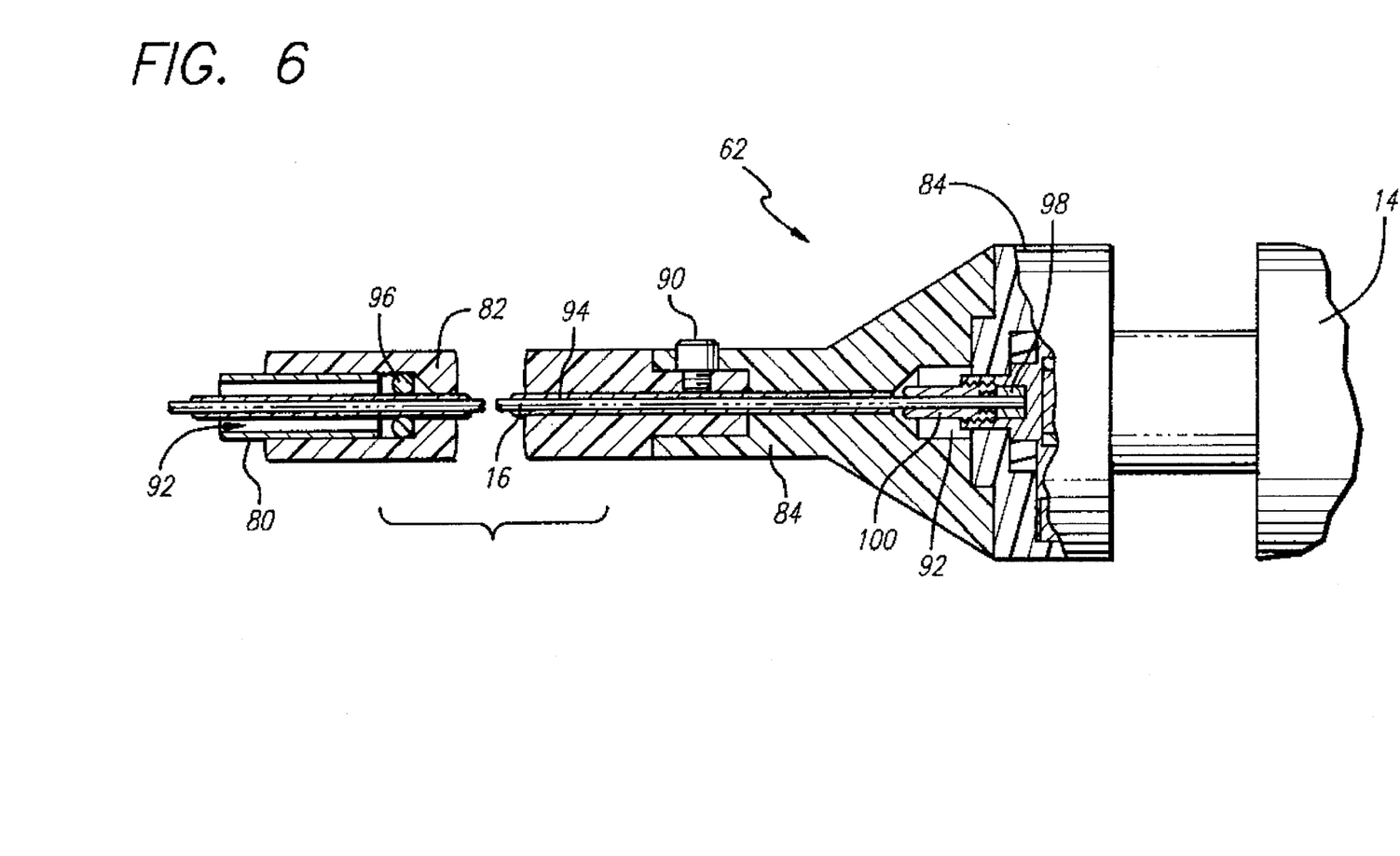
FIG. 6 is an enlarged longitudinal section view of one type of proximal connector assembly whereby the ultrasound delivering catheters of the present invention may be operatively connected to an ultrasound transducer.

One type of proximal connector assembly 62 which may be utilized is shown in detail in FIGS. 1 and 6. As shown, the proximal connector assembly 62 comprises a frontal body portion 80 a mid-body portion 82 and a rear body portion 84. The proximal end of the pliable catheter body 14 is received within the distal end of the frontal body portion 80 and is secured thereto by way of first nut 86. The proximal end of the frontal body portion 80 is inserted into the distal end of the mid-body portion 82 and is secured thereto by way of second nut 88. The proximal end of the mid-body portion 82 is inserted into the distal end of the rear body portion 84 and is secured thereto by set screw 90. A hollow longitudinal bore 92, of varying diameter, extends longitudinally through the frontal body portion 80, mid-body portion 82 and rear body portion 84 of the proximal connector assembly 62, thereby providing a passageway through which the ultrasound transmission member 16a extends from the proximal end of the pliable catheter body 14 to the point at which it is connected to the ultrasound transducer 14.

A ultrasound transmission member damping tube 94 is positioned axially within a portion of the hollow bore 92 of the proximal connector assembly 62 so as to surround a portion of the ultrasound transmission member 16 extending therethrough and to limit the potential for lateral side-to-side movement of the ultrasound transmission member 16 within the region thereof closest to its point of connection to the ultrasound transducer 14. The damping tubes 94 is held in place by abutment against the mid-body portion 82 and rear body portion 84 of the proximal connector assembly 62, as well as by O-ring 96 mounted within the bore 92 of the frontal body portion 80 of the proximal connector assembly 62.

The connection of the proximal end of the ultrasound transmission member 16 to the ultrasound transducer 14 is accomplished by way of a sonic connector assembly or apparatus disposed within the bore 92 of the rear body portion 84 of the connector assembly 62. Such sonic connector assembly or apparatus is configured and constructed to accomplish coupling of the ultrasound transmission member 16 to the horn of the ultrasound transducer 14, and to permit relatively unrestricted longitudinal forward/backward vibration or movement of the ultrasound transmission member 16, while substantially limiting the potential for lateral side-to-side vibration or movement thereof so as to avoid the likelihood of breakage or fracture of the ultrasound transmission member 16 in the region nearest its point of coupling to the horn of the ultrasound transducer 14. In the presently preferred embodiment, the sonic connector assembly or apparatus comprises a compressible gripping ferrule 98 having a small central aperture formed therethrough, through which the ultrasound transmission member 16 passes, as shown. A frontal member 100 is threadably tightened into the surrounding rigid body of the rear body portion 84 of the connector assembly 62 and serves to compress the gripping ferrule 98 inwardly onto the outer surface of the ultrasound transmission member 16, thereby gripping and holding the ultrasound transmission member 16 in its desired longitudinal position. The rear body portion 84 is further configured and constructed such that the proximal tip of the ultrasound transmission member 16 extends therethrough and is disposed within a depression formed on the proximal face of the rear body portion 84 so as to receive and couple with the horn 102 of the ultrasound transducer 14, as shown in FIG. 7. Thus, ultrasonic energy may be transmitted from the horn 102 of the ultrasound transducer 14 into the ultrasound transmission member 16 through which such energy may be transmitted longitudinally through the catheter 12 to the distal end thereof.

A coolant fluid infusion side arm 106 is formed on the proximal connector assembly 62 to permit infusion of a flow of coolant fluid into the bore 92 of the connector assembly 62, and through the lumen 46 of the catheter body 14a so as to bath the ultrasound transmission member 16 in coolant fluid, thereby preventing overheating of the ultrasound transmission member 16 during operation.

In accordance with the present invention, the distal tip member 18 of the catheter 12 may be configured and affixed to the distal end of the catheter body 14 in different ways as illustrated in the four (4) separate embodiments shown in FIGS. 2–5.

The distal tip member 18 utilized in each of the four (4) separate embodiments shown in FIGS. 2–5 share certain common structural characteristics with respect to the shape and configuration of the distal tip member 18, as well as the manner in which the distal tip member is connected to the distal end of the ultrasound transmission member 16 as shown, in each of the embodiments, the distal tip member 18 comprises a generally blunt conical or frusto conical distal portion 40 and a smaller diameter, generally cylindrical, proximal portion 42. The generally cylindrical proximal portion 42 is sized to be insertable into the distal end of the tubular catheter body 14 such that the distal tip of the tubular catheter body will abut against the annular shoulder 41 of the distal portion 40. A longitudinal guide wire passage bore 28 is formed eccentrically through the entire length of the distal tip member 18 such that a separate guide wire tube 54 may be passed through the catheter lumen 46 and through the guide wire passage bore 28. The distal end of the guide wire tube 54 is cut flush with the distal face of the distal portion 40a of the distal tip member 18, as shown. When so inserted, the guidewire tube 54 may be affixed or secured to the distal tip member 18 by heat sealing, adhesive or other suitable means, some of which are described herebelow in accordance with the four (4) specific embodiments of the present invention.

Also, an ultrasound transmission member receiving bore 60 extends longitudinally into a proximal portion of the distal tip member 18, terminating in a conical or pointed blind end point 61. The ultrasound transmission member receiving bore 60 is formed eccentrically in the distal tip member 18, apart from the location of the guidewire passage bore 28. The ultrasound transmission member receiving bore 60 is sized and configured to receive the distal-most portion of the ultrasound transmission member 16. In the embodiments shown, the extreme distal end 64 of the ultrasound transmission member 16 is advanced to a point where it abuts against the decreasing diameter of the blind conical end point 61 of the ultrasound transmission member receiving bore 60.

The ultrasound transmission member 16 may be fixed or engaged to the distal tip member 18 by any suitable means. For example, the ultrasound transmission member 16 may be initially cooled contracted by cooling prior to insertion into the bore 60, and subsequently allowed to thermally expand so as to frictionally engage the surrounding bore 60. Alternatively, the distal member 18 may be heated so as to expand the bore 60, prior to insertion of the distal portion of the ultrasound transmission member 16 into the bore 60. Thereafter, the bore 60 may be allowed to thermally shrink, thereby frictionally engaging the ultrasound transmission member 16. Alternatively, adhesive or welds may be utilized to secure the ultrasound transmission member 16 to the surrounding surfaces of the bore 60, thereby holding the distal tip member 18b in its desired position within the distal end of the catheter body 14 and additionally insuring a secure union between the ultrasound transmission member 16 and the distal tip member 18 such that ultrasonic vibration will be efficiently transmitted from the ultrasound transmission member 16 into the distal tip member 18.

As described herebelow, the distal tip member 18 may be specifically configured and affixed to the guidewire tube 54 and or catheter tube 14 by way of several different means, as incorporated in the four (4) separate embodiments shown in FIGS. 2–5 and described separately herebelow. Although these four (4) separate embodiments are described separately herebelow, it will be appreciated that the attributes and elements of each such embodiment may be combined in various permutations and combinations, without departing from the intended spirit and scope of the present invention.

ii. First Embodiment

Figure 2:
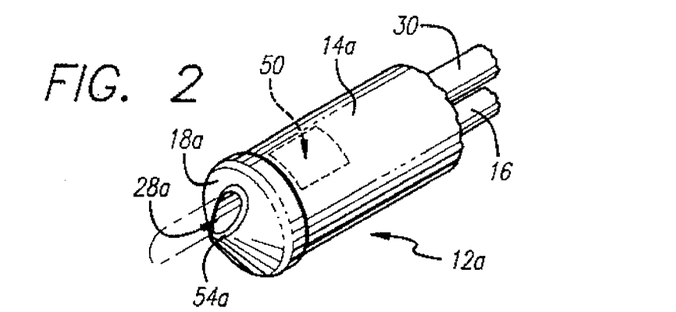
FIG. 2 is an enlarged perspective view of the distal portion of a first embodiment of an ultrasound delivering catheter of the present invention.
Figure 2A:
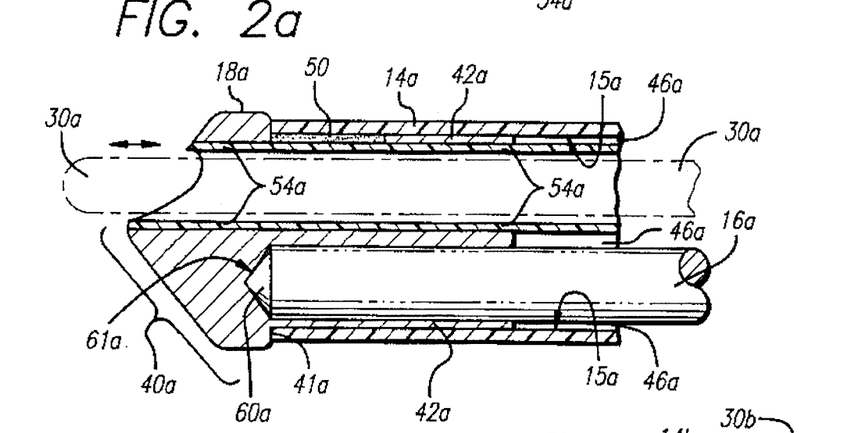
FIG. 2a is a longitudinal sectional view of FIG. 2.

In a first embodiment of the present invention, shown in FIGS. 2–2a, the a three way bond is formed between the distal portion of the catheter body 14a, the distal tip member 18a and the guidewire tube 54a, by providing an adhesive passage aperture 50 in the proximal portion 42a of the distal tip member 18a such that a quantity of adhesive may be disposed within such aperture 50, thereby bonding the inner surface 15a of the tubular guidewire body 14a to the outer surface of the guidewire tube 54a, while adhesively locking or holding the distal tip member. 18a in its desired position within the distal end of the catheter body 14a.

As shown in FIGS. 2–2a, the adhesive passage aperture 50 may be in the form of a single generally rectangular aperture formed in one side of the proximal portion 42a of the distal tip member 18a, extending from the outer surface of the proximal portion 42a, into the guidewire passage bore 28a formed therein. A quantity of adhesive may be initially disposed on the outer surface of the proximal portion 42a of the distal tip member 18a and/or within the confines of the aperture 50. Thereafter, the distal tip member 18a is inserted into the distal end of the tubular catheter body 14a, and the guidewire tube 54a is passed through the guidewire passage bore 28a. The quantity of adhesive which resides or flows through aperture 50, upon curing, will form a three way adhesive bond between the inner surface of the catheter body 14a, the proximal portion 42a of the distal tip member 18a and the outer surface of the guidewire tube 54a. Such three way bond serves to firmly hold the distal tip member 13a in its desired position while also preventing slippage or release of the guidewire tube 54a.

The adhesive utilized in this embodiment is preferably selected to be bondable with the material of the tubular catheter body 14a, distal tip member 18a and guidewire tube 54a. In most embodiments, adhesives such as cyanocarylic (Lock Tight™, Lock Tight Corporation, City, State) or polyurethane adhesives may be utilized. The soundness of the chemical adhesive bonding to the proximal portion 42a of the distal tip member 18a may be less critical than the soundness of the bonding to the inner surfaces of the adjacent tubular catheter body 14a and guidewire tube 54a, as the solidification or curing of the adhesive extending through the aperture 50 will frictionally or mechanically prevent movement of the distal tip member 18a, irrespective of any actual chemical boding between the adhesive and the material of which the proximal portion 42a of the distal tip member 18a is formed. Nonetheless, in many embodiments, it will be desirable to form the distal tip member 18a of metal, plastic, ceramic, or rubber, and to select an adhesive which also chemically bonds to the material of the distal tip member 18a, thereby adding to the soundness of the three-way bond formed thereby.

iii. Second Embodiment

Figures 3, 3A:
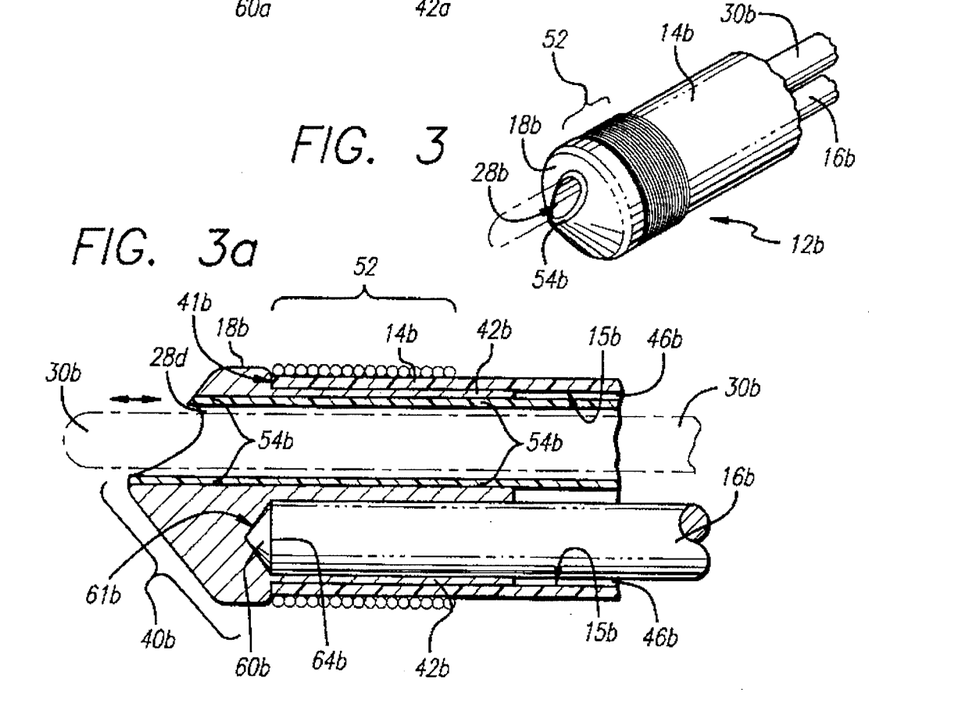
FIG. 3 is an enlarged perspective view of the distal portion of a second embodiment of an ultrasound delivery catheter of the present invention.
FIG. 3a is a longitudinal section view of FIG. 3.

As shown in FIGS. 3–3a, a second embodiment of a catheter 12b of the present invention comprises an elongate pliable tubular catheter body 14b having an inner luminal surface which defines a hollow lumen 46b extending longitudinally through the catheter body 14b. A rigid distal tip member 18b is inserted into the open distal end of the lumen 46b of the catheter body 14b and is secured thereto by way of a wire or other winding member 52 wound about the outer surface of the distal end of the catheter body 14b so as to exert inward compressive force against the catheter body 14b and distal head member 18b.

In the second embodiment of the catheter 12b, the distal head member 18b comprises a blunt conical or frusto-conical distal portion 40b and a generally cylindrical proximal portion 42b. The base of the distal portion 40b of the distal tip member 18b which abuts against the distal end of the catheter body 14b has an outer diameter which is no more than approximately two (2) millimeters different from the outer diameter of the adjacent distal end of the catheter body 14b, such that the outer surface of the distal portion 40b is substantially flush and continuous with the adjacent outer surface of the catheter body 14b. The cylindrical proximal portion 42b of the distal tip member 18b has an outer diameter which is substantially equal to the inner luminal diameter of the distal end of the catheter body 14b such that the cylindrical proximal portion 42b of the distal tip member 18b may be slideably inserted into the open distal end of the lumen 46b of the catheter body 14b. Thereafter, the wire or winding member 52 is repeatedly wound around the outer surface of the distal end of the catheter body 14b such that multiple convolutions or windings of the winding member 52 lie in side-by-side generally parallel relation to one another, as shown. The winding member 52 is wound about the outer surface of the catheter body 14b with sufficient tightness to exert enough compressive force against the underlying proximal portion 42b of the distal tip member 18b as to firmly hold the distal tip member 18b as to firmly maintain and affix the distal tip member 18b on the distal end of the catheter body 14b.

iv. Third Embodiment

Figures 4, 4A:
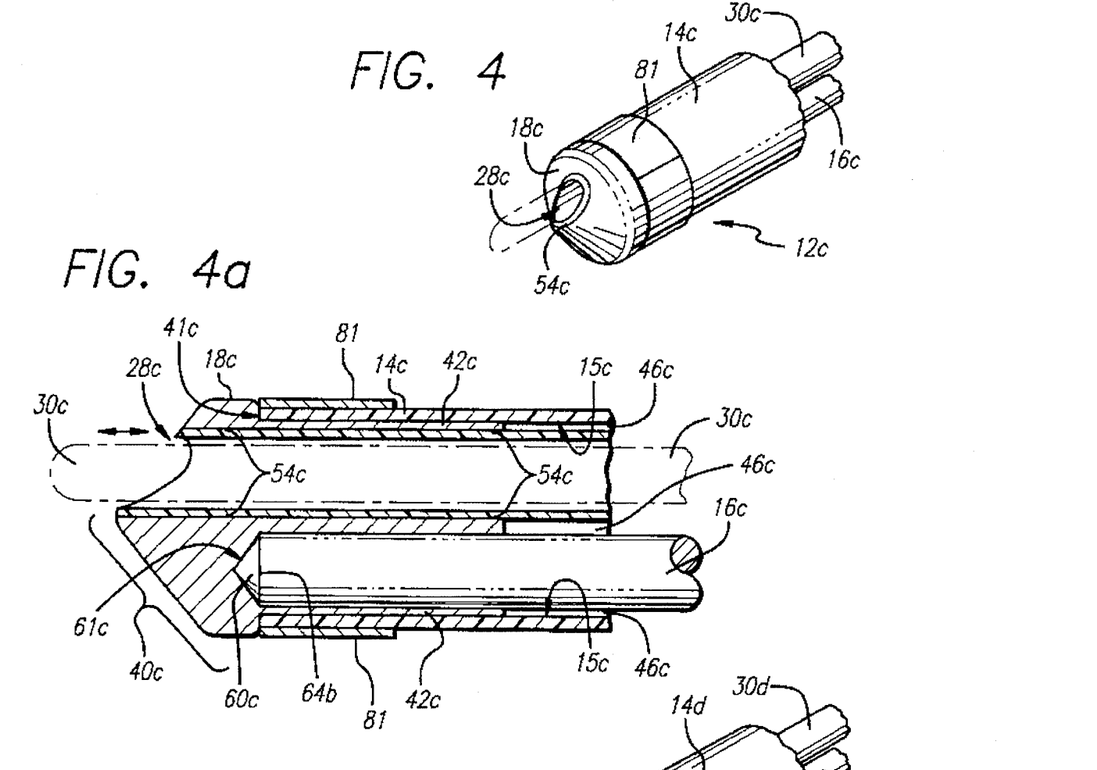
FIG. 4 is an enlarged perspective view of the distal portion of a third embodiment of an ultrasound delivery catheter of the present invention.
FIG. 4a is a longitudinal section view of FIG. 4.

As shown in FIGS. 4–4a, a third embodiment of the catheter 12c comprises an-elongate tubular catheter body 14c having an inner surface 15c which defines a hollow lumen 46c extending longitudinally through the catheter body 14c.

The distal tip member 18c comprises a rigid member having a blunt conical or frustoconical distal portion 40c and a generally cylindrical proximal portion 42c. The proximal portion 42c of the distal tip member 18c has a maximal outer diameter which is within approximately 2 millimeters of the outer diameter of the adjacent distal end of the catheter body 14c such that the distal portion 40c of the distal tip member 18c is substantially smooth and continuous with the adjacent outer surface of the distal end of the catheter body 14c. The proximal portion 42c of the distal tip member 18c has an outer diameter which is substantially the same as the inner diameter of the luminal surface 15c of the catheter body 14c such that the proximal portion 42c of the distal tip member 18c may be slideably inserted into the open distal end of the lumen 46c of the catheter body 14c and advanced therein to a point where the distal end of the catheter body 14c abuts against the larger-diameter distal portion 46c of the distal tip member 18c, as shown. After the distal tip member 18c has been so inserted into the distal end of the catheter body 14c a band member 81 is crimped or otherwise affixed about the outer surface of the catheter body 14c so as to exert inward compressive force on the distal end of the catheter body 14c and the underlying cylindrical proximal portion 42c of the distal tip member 18c, thereby firmly securing the distal tip member 18c to the distal end of the catheter body 14c.

v. Fourth Embodiment

Figures 5, 5A:
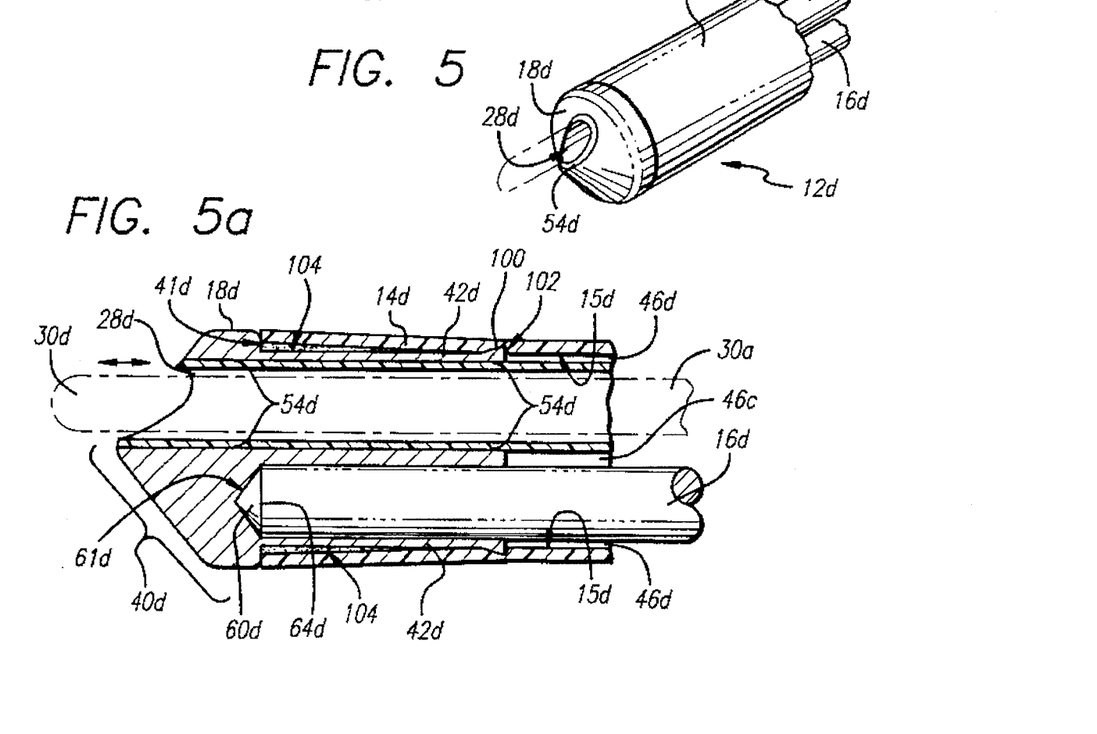
FIG. 5 is an enlarged perspective view of the distal portion of a fourth embodiment of an ultrasound delivery catheter of the present invention.
FIG. 5a is a longitudinal sectional view of FIG. 5.

As shown in FIGS. 5–5a a fourth embodiment of the catheter 12d comprises an elongate pliable catheter body 14b having an inner luminal surface 15d which defines a hollow lumen 46d extending longitudinally through the catheter body 14d.

The distal tip member 18d comprises a blunt conical or frustoconical distal portion 40d and a generally cylindrical proximal portion 42d having a chamfered or tapered outer surface configuration and, optionally, one or more barbs or engagement projections 100 extending outwardly therefrom to fictionally engage the inner luminal surface 15d of the catheter body 14d. Optionally, a corresponding depression 102 may be formed about the luminal surface 15d of the catheter body 14d, said groove or depression 102 being positioned and configured to receive the engagement projection 100 of the distal tip member 18d therein.

The outer surface of the proximal portion 42d of the distal tip member 18d is preferably chamfered or tapered such that the diameter of the proximal portion 14d is largest at its proximal-most point and smallest at its distal-most point. As shown, such chamfering or tapering of the proximal portion 42d causes part of the proximal portion 42d to be smaller in outer diameter than the adjacent inner luminal surface 15d of the catheter body 14d, thereby resulting in a gap or space 104 between the outer surface of part of the proximal portion 42d, and the adjacent inner surface 15d of the distal end of the catheter body 14d. A quantity of adhesive may be applied to the outer surface of the proximal portion 42d of the distal tip member 18d prior to its insertion into the open distal end of the lumen 46d of the catheter body 14d, such that the adhesive will be disposed within the gap or space 104 formed between the outer-surface of the proximal portion 42d of the distal tip member 18d and the inner surface 15d of the catheter body 14d when the distal tip member 18d is fully inserted thereinto. Such adhesive within the gap or space 104 will adhesively bond at least part of the outer surface of the proximal portion 42d to the adjacent inner surface 15d of the catheter body 14d.

The adhesive disposed within gap or space 104 will be selected to form an adhesive bond between the material of the catheter body 14d and that of the distal tip member 18d.

Although the invention has been described hereabove with respect to four separate embodiments, it will be appreciated that, although each of said four embodiments may be utilized separately, such four embodiments may also be combined in all available combinations thereof to facilitate optimal bonding and affixation of the distal tip member 18 to the catheter body 14 and/or guidewire passage tube 54.

Furthermore, it will be appreciated that, although the present invention has been described herein with respect to presently preferred embodiments of the invention, various modifications, alterations, additions and deletions may be made to such above-described embodiments without departing from the intended spirit and scope of the invention. All such modifications, additions, deletions and alterations shall be included within the scope of the following claims. In this embodiment, the combination of the adhesive bond formed by the adhesive disposed within the gap or space 104, and the interaction of the engagement projections 100 with the adjacent inner surface 15d of the catheter body 14d, or the optional receiving groove or depression 102, combines to result in firm affixation of the distal tip member 18b to the distal end of the catheter body 14b.

What is claimed is:

1. An ultrasound catheter for delivering ultrasonic energy from an extracorporeally positioned ultrasound generating apparatus, to a treatment location within a mammalian body, said catheter comprising:

a tubular catheter body having a proximal end, a distal end and a lumen extending longitudinally therethrough, said lumen having an inner luminal surface;

a distal head member at least partially inserted into the distal end of said catheter lumen, the portion of said distal head member which inserts into the distal end of said catheter lumen having an outer surface which abuts against the inner luminal surface of the catheter body;

an ultrasound transmission member extending longitudinally through said catheter body, said ultrasound transmission member having a distal end in contact with said distal head member and a proximal end which is connectable to said extracorporeally positioned ultrasound generating apparatus; and a pressure exerting member mounted around the distal end of the catheter body to exert inward compressive force against the distal end of the catheter body and the portion of the distal head member received therewithin to retain said proximal portion of the distal head member within the lumen of said catheter body.

2. The catheter of claim 1 wherein the distal head member comprises a guidewire passage bore, and wherein a guidewire guide tube extends through at least a portion of said catheter body and through the guidewire passage bore formed in said distal head member, and wherein:

at least one adhesive passage aperture is formed in the portion of said distal head member which inserts into the distal end of said catheter lumen, said aperture forming a passageway from said outer surface of said distal head member into said guidewire passage bore such that adhesive may pass through said aperture to form a three way bond between the guidewire tube which extends through said guidewire bore, said distal head member and the adjacent luminal surface of said catheter body.

3. The catheter of claim 2 wherein an annular pressure exerting member is mounted around the distal end of the catheter body to exert inward compressive force against the distal end of the catheter body and the portion of the distal head member disposed therewithin.

4. The catheter of claim 1 wherein said pressure exerting member comprises a winding member wound around the outer surface of the distal end of said catheter body.

5. The catheter of claim 4 wherein said pressure exerting member comprises a winding member wound around the outer surface of the distal end of said catheter body.

6. The catheter of claim 1 wherein said pressure exerting member comprises a wire wound around the distal end of the catheter body.

7. The catheter of claim 3 wherein said pressure exerting member comprises a wire wound around the distal end of the catheter body.

8. The catheter of claim 1 wherein said pressure exerting member comprises a band extending around the outer surface of the distal end of the catheter body.

9. The catheter of claim 3 wherein said pressure exerting member comprises a band extending around the outer surface of the distal end of the catheter body.

10. The catheter of claim 1 wherein the portion of the distal head member that is disposed within the distal end of said lumen has at least one projection formed thereon to frictionally engage the adjacent luminal surface of the catheter body.

11. The catheter of claim 2 wherein the portion of the distal head member that is disposed within the distal end of said lumen has at least one projection formed thereon to frictionally engage the adjacent luminal surface of the catheter body.

12. The catheter of claim 10 wherein the catheter engaging projection comprises a barb.

13. The catheter of claim 11 wherein the catheter engaging projection comprises a barb.

14. The catheter of claim 10 wherein a corresponding depression is formed in the luminal surface of said catheter body, said depression being positioned and configured to receive and frictionally engage said catheter projection.

15. The catheter of claim 11 wherein a corresponding depression is formed in the luminal surface of said catheter body, said depression being positioned and configured to receive and frictionally engage said catheter projection.

16. The catheter of claim 1 wherein the portion of the distal head member disposed within the distal end of the lumen has a tapered outer surface, a portion of said tapered outer surface having an outer diameter smaller than the diameter of the adjacent lumen so as to create an adhesive containment space between the outer surface of the distal head member and the adjacent luminal surface of the catheter body, an adhesive being disposed within said space to adhesively bond said distal head member to said catheter body.

17. The catheter of claim 1 wherein a hollow receiving bore is formed longitudinally into a proximal portion of said distal head member, and wherein a distal portion of said ultrasound transmission member extends into said receiving bore, in abutting contact with said distal head member.

18. The catheter of claim 17 wherein the distal portion of said ultrasound transmission member which extends into said receiving bore contacts and frictionally engages the surrounding surface of the distal head member.

19. The catheter of claim 18 wherein said frictional engagement is by thermal shrinkage of the distal head member after the ultrasound transmission member has been inserted into said bore.

20. The catheter of claim 18 wherein said frictional engagement is by expansion of said ultrasound transmission member after it has been inserted into said bore.

21. The catheter of claim 17 wherein said ultrasound transmission member is affixed to said distal head by weldment.

22. The catheter of claim 17 wherein said ultrasound transmission member is affixed to said distal head by adhesive.

23. A catheter for delivering ultrasound from an extracorporeally positioned ultrasound generating device to a location within a mammalian body, said catheter comprising:

an elongate flexible catheter body having a proximal end, a distal end and at least one lumen extending longitudinally therethrough, said lumen having an inner luminal surface;

an ultrasound transmission member having a proximal end and a distal end, said ultrasound transmission member extending longitudinally through the lumen of said catheter body the distal end of said ultrasound transmission member terminating adjacent the distal end of said catheter body, the proximal end of said ultrasound transmission member being connectable to said ultrasound generating device;

a distal head member at least partially inserted into the distal end of the lumen of said catheter body and affixed thereto so as to remain in concomitant contact with a) the distal end of said catheter body and b) the distal end of said ultrasound transmission member, said distal head member comprising:

i) a distal portion having a blunt conical configuration and an annular shoulder configured to abut against the distal end of said catheter body; and ii) a generally cylindrical proximal portion extending proximally from said distal portion, said generally cylindrical proximal portion being received within the distal end of the lumen of said catheter body and in abutment with the adjacent luminal surface of said catheter body;

iii) a guidewire passage bore extending longitudinally through said distal portion and said proximal portion, a guidewire tube extending through said bore and into said catheter body;

iv) at least one adhesive passage aperture being formed in said proximal portion, said aperture forming a passageway from the outer surface of said proximal portion into said guidewire bore such that adhesive which passes through said aperture may concomitantly bond to the luminal surface of said catheter body and the guidewire tube which extends through said guidewire bore.

24. The catheter of claim 23 further comprising an annular pressure exerting member mounted around the distal end of the catheter body to exert inward compressive force against the distal end of the catheter body and the portion of the distal head member disposed therewithin.

25. The catheter of claim 23 wherein said pressure exerting member comprises a winding member wound around the outer surface of the distal end of said catheter body.

26. The catheter of claim 25 wherein said winding member comprises a wire.

27. The catheter of claim 24 wherein said pressure exerting member comprises a band.

28. The catheter of claim 23 wherein at least one projection is formed on the portion of the distal head member disposed within the distal end of said lumen, said projection being sized and configured to frictionally engage the adjacent luminal surface of said catheter body.

29. The catheter of claim 28 wherein said projection comprises a barb.

30. The catheter of claim 28 wherein a corresponding depression is formed in the luminal surface of said catheter body, said depression being positioned and configured to receive and frictionally engage said projection.

31. The catheter of claim 23 wherein the portion of the distal head member disposed within the distal end of the lumen has a tapered outer surface, a portion of said tapered outer surface having an outer diameter smaller than the diameter of the adjacent lumen so as to create an adhesive containment space between the outer surface of the distal head member and the adjacent luminal surface of the catheter body, an adhesive being disposed within said space to adhesively bond said distal head member to said catheter body.

32. The catheter of claim 23 wherein a receiving bore is formed longitudinally into a proximal portion of said distal head member and wherein a distal portion of said ultrasound transmission member extends into said receiving bore, in abutting contact with said distal head member.

33. The catheter of claim 32 wherein the distal portion of the ultrasound transmission member which extends into said receiving bore is sized and configured to contact and frictionally engage the surrounding surface of the distal head member.

34. The catheter of claim 33 wherein said frictional engagement is by thermal shrinkage of the distal head member after the ultrasound transmission member has been inserted into said bore.

35. The catheter of claim 34 wherein said frictional engagement is by expansion of said ultrasound transmission member after said ultrasound transmission member has been inserted into said bore.

36. The catheter of claim 23 wherein said ultrasound transmission member is affixed to said distal head member by weldment.

37. The catheter of claim 23 wherein said ultrasound transmission member is affixed to said distal head member by adhesive.

38. A catheter for delivering ultrasound from an extracorporeally positioned ultrasound generating device to a location within a mammalian body, said catheter comprising:

an elongate flexible catheter body having a proximal end, a distal end and at least one lumen extending longitudinally therethrough, said lumen having an inner luminal surface;

an ultrasound transmission member having a proximal end and a distal end, said ultrasound transmission member extending longitudinally through the lumen of said catheter body the distal end of said ultrasound transmission member terminating adjacent the distal end of said catheter body, the proximal end of said ultrasound transmission member being connectable to said ultrasound generating device;

a distal head member at least partially inserted into the distal end of the lumen of said catheter body and affixed thereto so as to remain in concomitant contact with a) the distal end of said catheter body and b) the distal end of said ultrasound transmission member, said distal head member comprising:

i) a distal portion having a blunt conical configuration and an annular shoulder configured to abut against the distal end of said catheter body; and ii) a generally cylindrical proximal portion extending proximally from said distal portion, said generally cylindrical proximal portion being received within the distal end of the lumen of said catheter body and in abutment with the adjacent luminal surface of said catheter body;

iii) at least one pressure exerting member positioned around the outer surface of the distal end of the catheter body to exert inward compressive force to frictionally retain the proximal portion of the distal head member within the lumen of said catheter body.

39. The catheter of claim 38 wherein said pressure exerting member comprises a winding member wound around the outer surface of the distal end of said catheter body.

40. The catheter of claim 39 wherein said winding member comprises a wire.

41. The catheter of claim 38 wherein said pressure exerting member comprises a band extending around the outer surface of the distal end of the catheter body.

42. The catheter of claim 38 wherein a projection is formed on the proximal portion of said distal head to frictionally engage the adjacent luminal surface of the catheter body.

43. The catheter of claim 42 wherein said projection comprises a barb.

44. The catheter of claim 42 wherein a corresponding depression is formed in the luminal surface of said catheter body, said depression being positioned and configured to receive and frictionally engage said projection.

45. The catheter of claim 38 wherein a hollow receiving bore is formed longitudinally into the proximal portion of the distal head member, and wherein a distal portion of said ultrasound transmission member extends into said receiving bore, in abutting contact with said distal head member.

46. The catheter of claim 45 wherein the distal portion of said ultrasound transmission member which extends into said receiving bore is sized and configured to contact and frictionally engage the surrounding surface of the distal head member.

47. The catheter of claim 46 wherein said frictional engagement is by thermal shrinkage of the distal head member after the ultrasound transmission member has been inserted into said bore.

48. The catheter of claim 46 wherein said frictional engagement is by expansion of said ultrasound transmission member after said ultrasound transmission member has been inserted into said bore.

49. The catheter of claim 38 wherein said ultrasound transmission member is affixed to said distal head by weldment.

50. The catheter of claim 38 wherein said ultrasound transmission member is affixed to said distal head by adhesive.

51. The catheter of claim 38 wherein a guidewire passage bore extends longitudinally through said distal head member and a guidewire tube extends through said guidewire passage bore and through at least a portion of said catheter body, and wherein:

an adhesive aperture is formed in the proximal portion of said distal head member extending from the outer surface thereof into said guidewire bore such that adhesive may pass through said aperture to form a three-way bond between said guidewire tube, said distal head member and the adjacent luminal surface of said catheter body.

52. A catheter for delivering ultrasound from an extracorporeally positioned ultrasound generating device to a location within a mammalian body, said catheter comprising:

an elongate flexible catheter body having a proximal end, a distal end and at least one lumen extending longitudinally therethrough, said lumen having an inner luminal surface;

an ultrasound transmission member having a proximal end and a distal end, said ultrasound transmission member extending longitudinally through the lumen of said catheter body the distal end of said ultrasound transmission member terminating adjacent the distal end of said catheter body, the proximal end of said ultrasound transmission member being connectable to said ultrasound generating device;

a distal head member at least partially inserted into the distal end of the lumen of said catheter body and affixed thereto so as to remain in concomitant contact with a) the distal end of said catheter body and b) the distal end of said ultrasound transmission member, said distal head member comprising:

i) a distal portion having a blunt conical configuration and an annular shoulder configured to abut against the distal end of said catheter body; and ii) a generally cylindrical proximal portion extending proximally from said distal portion, said generally cylindrical proximal portion being received within the distal end of the lumen of said catheter body and in abutment with the adjacent luminal surface of said catheter body;

iii) said generally cylindrical proximal portion having a tapered outer surface, a portion of said tapered outer surface having an outer diameter smaller than the diameter of the adjacent catheter lumen so as to create an adhesive containment space between the outer surface of the proximal portion of the distal head member and the adjacent luminal surface of the catheter body, an adhesive being disposed within said space to adhesively bond said distal head member to said catheter body.

53. The catheter of claim 52 wherein the generally cylindrical proximal portion of the distal head member further comprises:

a projection extending from said proximal portion of said distal head member to frictionally engage the adjacent luminal surface of the catheter body.

54. The catheter of claim 53 wherein said projection comprises a barb.

55. The catheter of claim 53 further comprising: a depression formed in the luminal surface of said catheter body, said depression being positioned and configured to receive and frictionally engage said projection.

56. The catheter of claim 52 further comprising: at least one pressure exerting member positioned around the outer surface of the distal end of the catheter body to exert inward compressive force to frictionally retain the proximal portion of the distal head member within the lumen of said catheter body.

57. The catheter of claim 56 wherein pressure exerting member comprises a winding member wound around the outer surface of the distal end of said catheter body.

58. The catheter of claim 57 wherein said winding member comprises a wire.

59. The catheter of claim 56 wherein said pressure exerting member comprises a band extending around the outer surface of the distal end of the catheter body.

60. The catheter of claim 52 wherein a hollow receiving bore is formed longitudinally into the proximal portion of the distal head member, and wherein a distal portion of said ultrasound transmission member extends into said receiving bore in abutting contact with said distal head member.

61. The catheter of claim 60 herein the distal portion of the ultrasound transmission member which extends into said receiving bore is sized and configured to contact and frictionally engage the surrounding surface of the distal head member.

62. The catheter of claim 61 wherein said frictional engagement is by expansion of said ultrasound transmission member after said ultrasound transmission member has been inserted into said bore.

63. The catheter of claim 52 wherein ultrasound transmission member is affixed to said distal head by weldment.

64. The catheter of claim 52 wherein said ultrasound transmission member is affixed to said distal head by adhesive.

65. The catheter of claim 52 wherein a guidewire passage bore extends longitudinally through said distal head member and a guidewire tube extends through said guidewire passage bore and through at least a portion of said catheter body, and wherein:

an adhesive aperture is formed in the proximal portion of said distal head member extending from the outer surface thereof into said guidewire bore such that adhesive may pass through said aperture to form a three-way bond between said guidewire tube, said distal head member and the adjacent luminal surface of said catheter body.

* * * * *

UNITED STATES PATENT AND TRADEMARK OFFICE
CERTIFICATE OF CORRECTION

PATENT NO. : 5,542,917
DATED : August 6, 1996
INVENTOR(S) : Henry Nita, Timothy Mills It is certified that error appears in the above-indentified patent and that said Letters Patent is hereby corrected as shown below:

Cover Page Figure, Change "16", To Read --116--.

Cover Page Figure, Change "14" [located between "10" and "84" only], To Read --114--.

Cover Page Figure, Change "26", to read --16--.

FIG. 1, Change "16", To Read --116--.

FIG. 1, change "26", To Read --16--.

FIG. 1, Change "14" [located between "10" and "84" only], To Read -114--.

FIG. 6, Change "14", To Read --114--.

Column 3, Lines 39, 53, 55, 57 and 63 [two occurrences], Change "14", To Read --114--.

Column 3, Line 59, Change "16", to Read -116--.

Column 4, Line 5, Change "14", To Read --114--.

UNITED STATES PATENT AND TRADEMARK OFFICE
CERTIFICATE OF CORRECTION

PATENT NO. : 5,542,917
DATED : August 6, 1996
INVENTOR(S) : Henry Nita, Timothy Mills It is certified that error appears in the above-indentified patent and that said Letters Patent is hereby corrected as shown below:

Column 5, Lines 28, 48, 56 and 63, After "Transducer",
  Change "14", To Read --114--.

Column 6, Lines 2, 9, 26 and 28, After "Transducer",
  Change "14", To Read --114--.

Column 7, Line 56, Change "tubular guidewire body",
  To Read --catheter body--.

Column 8, Line 10, Change "13a", To Read --18A--.

Signed and Sealed this

Third Day of June, 1997

Attest:

BRUCE LEHMAN

Attesting Officer        Commissioner of Patents and Trademarks